US007229404B2

(12) United States Patent
Bouffier

(10) Patent No.: US 7,229,404 B2
(45) Date of Patent: Jun. 12, 2007

(54) SURGICAL PROSTHESIS-FORMING DEVICE USED TO IMPLANT AN ORGAN SUPPORT IN A MAMMAL

(76) Inventor: Bernard Bouffier, 23 Rue des Grands Essarts, F-25480 Ecole (FR)

( * ) Notice: Subject to any disclaimer, the term of this patent is extended or adjusted under 35 U.S.C. 154(b) by 76 days.

(21) Appl. No.: 10/524,861

(22) PCT Filed: Aug. 27, 2003

(86) PCT No.: PCT/FR03/02589

§ 371 (c)(1),
(2), (4) Date: Feb. 15, 2005

(87) PCT Pub. No.: WO2004/019813

PCT Pub. Date: Mar. 11, 2004

(65) Prior Publication Data

US 2005/0261547 A1    Nov. 24, 2005

(30) Foreign Application Priority Data

Aug. 30, 2002 (FR) .................................. 02 10761

(51) Int. Cl.
*A61F 2/02* (2006.01)
(52) U.S. Cl. .......................................... 600/30; 600/37
(58) Field of Classification Search .................. 600/29, 600/30, 37, 121, 149
See application file for complete search history.

(56) References Cited

U.S. PATENT DOCUMENTS

| 5,713,829 | A | 2/1998 | Hakky et al. | |
|---|---|---|---|---|
| 6,599,235 | B2 * | 7/2003 | Kovac | 600/30 |
| 6,908,473 | B2 * | 6/2005 | Skiba et al. | 606/198 |
| 2002/0143234 | A1 * | 10/2002 | LoVuolo | 600/30 |

FOREIGN PATENT DOCUMENTS

| EP | 1 159 920 | 12/2001 |
|---|---|---|
| WO | WO 94/26215 | 11/1994 |
| WO | WO 02/30293 | 4/2002 |

* cited by examiner

*Primary Examiner*—Charles A. Marmor, II
*Assistant Examiner*—Christine D. Hopkins
(74) *Attorney, Agent, or Firm*—Lucas & Mercanti, LLP

(57) ABSTRACT

The invention concerns a surgical device forming a surgical prosthesis.

This device is characterized in that it contains at least one first sling (20), at least one first traction component (30), and at least one first fixation or anchoring system (40), designed to work in concert with at least said first traction component (30), which includes a cage-forming device (42), the upper end (43) of which is fitted with a sliding component (46) which makes it easier to pull on the traction component (30) which acts on the sling (20), so that said pulling effects translation of one end of the sling (20).

The device is preferably intended for the treatment of urinary incontinence in female mammals, in particular the human female.

20 Claims, 2 Drawing Sheets

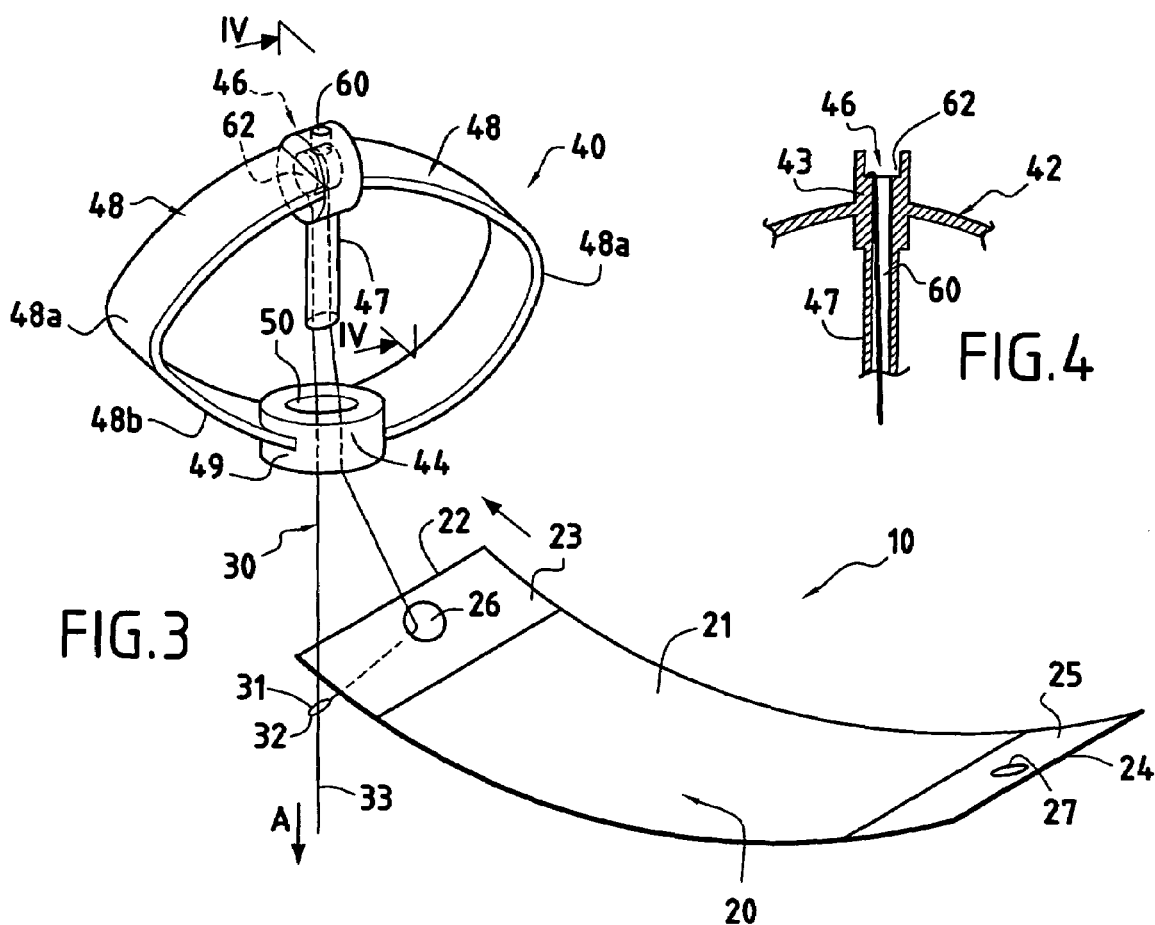
FIG.3
FIG.4
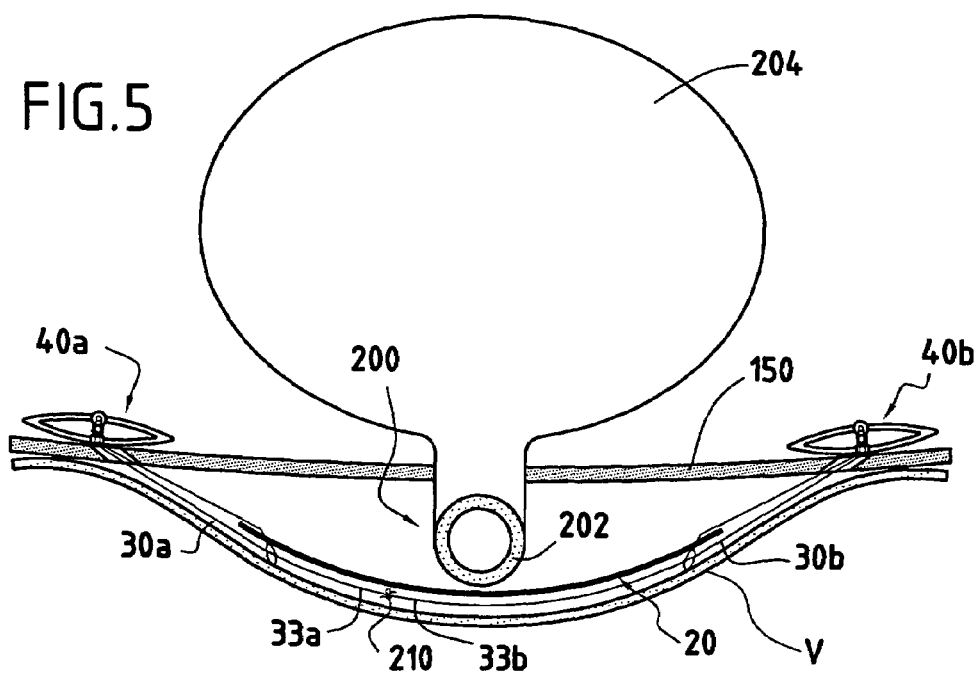
FIG.5

SURGICAL PROSTHESIS-FORMING DEVICE USED TO IMPLANT AN ORGAN SUPPORT IN A MAMMAL

This invention essentially concerns a surgical instrument forming a surgical prosthesis, designed to effect the implantation of a means of support for a mammalian organ. Within the scope of the invention, any mammalian organ which can be supported can be treated using the surgical instrument according to the invention. The invention is particularly suitable for the support of pelvic organs: the urethra, the bladder, the vagina, the cervix of the uterus, the uterus and the rectum. The invention preferably concerns a surgical instrument forming a surgical prosthesis to support the urethra in treatment of urinary incontinence, in particular in female mammals and preferably in the human female.

The instrument corresponding to a surgical prosthesis according to this invention can be used to fix or keep in place various different tissues or organs, with more or less significant modifications as dictated by anatomical and pathological considerations.

STATE OF THE ART

It is known that stress urinary incontinence is the consequence of excessive displacement of the urethra when pressure is generated within the abdomen as a result of coughing, laughing, physical exertion or, more generally, any form of abdominal strain.

The greater the mobility of the urethra, the more likely and the more copious the leakage of urine, to the point that the canal may be in a permanent state of ptosis.

The incontinence may be associated with a variable degree of prolapse of the organs of the pelvis (i.e. the vagina, the uterus, the bladder or the rectum), or it may be uncomplicated. It is in almost all cases the result—more or less delayed—of vaginal delivery.

It is a major problem which seriously compromises the freedom and dignity of mothers. The fact that it is often kept secret makes it difficult to study the associated morbidity.

On the other hand—and this is an important point—it is not a fatal disease so its treatment is essentially symptomatic, with the physician under the onus of seeking a perfect, complication-free outcome with the least aggressive modalities possible.

A first step forward was made with the development of the so-called TVT (Tension-free Vaginal Tape) which represents a modern version of the strip traditionally used to support the urethra from underneath. The innovation consists in producing the band in polypropylene, a well-characterized material, especially in hernial prostheses. Moreover, the implantation procedure for such a device is minimally invasive.

Document EP-A-0 248 544 describes an instrument corresponding to a surgical prosthesis to correct female incontinence, consisting of a body made of a cross-linked synthetic polymer hydrogel with some form of local reinforcement such as a netting made of plastic, e.g. polypropylene (see column 3, lines 39 to 46).

The body of the device is suspended by means of either sutures inserted in para-urethral pelvic tissue or using a long needle at the anterior abdominal wall (column 4, lines 1 to 19, and FIGS. 2 to 4).

Furthermore, documents U.S. Pat. No. 5,899,909 and WO 02/30293 describe an instrument and a treatment procedure for female urinary incontinence, and in particular a surgical implant comprising a strip designed to be positioned below the urethra to prevent incontinence, said strip working in concert with two wires joined to each end of the strip, connected opposite the strip to a needle-shaped anchoring device, and crossing the tissue of the abdominal wall or of the pelvic wall (rectus sheath).

Application WO 98/35632 relates to other embodiments of tension strips with reinforcement at the ends provided by folding over of the edges of the strip on themselves, thereby doubling the thickness at those points. These can be anchored on the pelvic bone.

Such devices give very good outcomes but the implantation procedure is highly invasive because of the size of the two needles used and the tissue damage entailed by their passage.

The unacceptable incidence of complications and mortality associated with this kind of procedure has attracted extensive media attention, especially in France, and the modality has not significantly spread in other countries. In practice, the procedure is not easily reproducible and the operator learning curve is not as steep as might have been hoped.

PURPOSE OF THE INVENTION

The main purpose of this invention is to resolve the current technical problem by making available a surgical device forming a surgical prosthesis to immobilize and support a physiological organ, notably to support the urethra to correct urinary incontinence, in particular in female mammals, preferably human females, the implantation of said device being a less aggressive procedure than that for prior devices thus cutting down or more or less eliminating the risk of serious complications.

Another main purpose of this invention is to resolve the current technical problem by making available a surgical device forming a surgical prosthesis to immobilize and support any mammalian organ which can be supported, which might particularly advantageously be adapted to the support of pelvic organs such as the urethra, the bladder, the vagina, the uterine cervix, the uterus and the rectum.

Another main purpose of this invention is to resolve the current technical problem by means of a device which can be implanted in a surgical procedure to provide immobilization and support in a short operation which can be performed under local anesthesia without the need for either admission into a hospital setting or post-operative bed-rest, and which can therefore be performed in an outpatient context.

This invention makes it possible for the first time to resolve these technical problems in a simple, reliable way which is reproducible at the industrial and medical scales, simplifying the surgical procedure by making it possible to perform the implantation operation under local anesthesia without either admission into hospital or post-operative bed-rest.

Thus, according to a first aspect, this invention provides a surgical device forming a surgical prosthesis designed to provide support to a mammalian organ that can be supported, notably to correct urinary incontinence, characterized in that it comprises:

a) at least one first support component to provide support of elongated shape defining a first and a second end, designed to exert a supporting action on said physiological organ; said first support component being made at least partially of a substantially inextensible but flexible and deformable material;

b) at least one first traction component, advantageously filiform, which can be connected at least temporarily with at least one end of said first elongated support component, made of a substantially inextensible material, which allows the pulling and maintenance in place of said first elongated sling in such a position that it can provide said support;

c) at least one first immobilization or anchoring system, designed to work in concert with said first traction component, inextensible, in such a way as to allow the fixation and maintenance in place of said first elongated sling.

Said first anchoring system comprises a device which forms a cage with an upper end and a lower end, the upper end being fitted with a sliding component which facilitates pulling on the traction component which acts on the elongated sling to effect—through said pulling—the translation of one end of the elongated sling in order to provide support to said organ and/or to keep said organ in position.

According to an advantageous embodiment of the invention, said lower end of the anchoring system is configured to be inserted on or attached to a mammalian substrate which is relatively resistant to tearing, e.g. bone or some other appropriate tissue. In the case of an embodiment to provide support to correct urinary incontinence, the lower end of the anchoring system is preferably inserted on the pubic bone, or on the tissue of the wall of the hypogastrium, the pelvic cavity, or possibly the abdomen.

According to another advantageous embodiment of the invention, the upper part and the lower part of the cage-forming component of the anchoring system are joined to one another by several lateral bridging arms made of a substantially inextensible but flexible and deformable material.

Advantageously, said lateral bridging arms are long enough to substantially form a kink at their mid-point, in such a way that the upper part folds back in the direction of the lower part with the part of the arm joined to the lower part thus being also inserted on the above-mentioned mammalian substrate which is relatively resistant to tearing, e.g. bone or some other appropriate tissue. Thus the anchoring system is inserted on a large area of the mammalian substrate which is resistant to tearing, thereby further restricting or preventing tearing thereof: this is particularly advantageous if the substrate on which it is inserted includes mammalian tissue, and in particular if it concerns the tissue of the wall of the hypogastrium, the pelvic cavity or possibly the abdomen.

According to an advantageous embodiment of the invention, the cage-shaped sliding component of the anchoring system is configured so as to act like a pulley, around which the traction component can slide or translate to pull on the elongated sling.

According to a particularly advantageous embodiment of the invention—which is patentable in and of itself—the traction component is in the form of a traction wire, preferably including a sliding component such as a ring or a loop at one end. The other end of the wire—the free end—can be inserted into this ring or loop in such a way as to create a lasso-like loop device to facilitate pulling on the elongated sling. In this case, the elongated sling preferably has at least one hole through which said traction wire can be passed to be trapped by the lasso-type device so that, when the other end of the wire—the free end—is pulled on, the result is the translation of said end of the elongated sling (e.g. a strip).

According to another particularly advantageous embodiment of the invention, the device could be configured so that both ends of the elongated sling (e.g. a strip) could be pulled on simultaneously by a single anchoring system.

Moreover, a first anchoring system joined to one end of the elongated sling (e.g. a strip) could be configured to allow fixation at a predetermined, set position, while the other end of the elongated sling (e.g. a strip) is joined to a second anchoring system according to the present invention, thereby allowing displacement of the second end—here again mobile—of the elongated sling in order to exert the desired traction on the mammalian organ as required.

According to another embodiment of the invention, the above-mentioned cage-forming device includes at its upper end a hollow, tubular component, one end of which is designed to be joined to or continuous with the upper part of the cage and, at the same time, to form the sliding component, in particular by presenting a surface which forms the pulley around which the traction wire is designed to slide; advantageously, said end has a hole which is coaxial with the hollow tubular component.

According to yet another embodiment of the invention, the lower part of at least the first anchoring system or each anchoring system can include an annular part defining a central opening through which can be inserted a first traction component—advantageously filiform as mentioned above—or each traction component. This annular part can also advantageously be used to insert the needle of a trocar to penetrate into the tissue.

Moreover, according to another advantageous embodiment, the upper part of at least one first anchoring system or of each anchoring system can contain a hole through which the needle of a trocar can be inserted to penetrate the tissues. Thus, each anchoring system can be put in position in a safe, reliable way inside a trocar between the trocar's penetrating needle and an external sheath, in a direction which is substantially axial to the anchoring system, as will be easily understood by those skilled in the art, especially with reference to the appended FIG. 2 which will be described below.

According to a second aspect, this invention also covers as a novel, separately patentable product, the traction component itself as defined above or as resulting from the following description, taken with reference to the drawings which represent an integral part of this invention and illustrate the description.

According to a particular modified embodiment of the invention, the first elongated sling is in the shape of a strip, of which at least that part which is located between its ends consists of a fabric or meshwork created from one or more wires made of a substantially inextensible but flexible and deformable material.

Advantageously, the material used to make the wire or wires comprising the fabric of the strip is an organic polymer which is compatible with implantation in mammalian tissue, this organic material being advantageously one of the group of polyethylene, polypropylene or nylon and preferably polypropylene.

According to another modified embodiment of the invention, the first and/or the second filiform traction component includes or consists of an inextensible traction wire, in particular a wire made of some inextensible material, e.g. an organic polymer which is compatible with long-term implantation into mammalian tissue, in particular polyethylene, polypropylene or nylon.

According to a third aspect, this invention also covers as a novel, separately patentable product, each fixation or anchoring system as defined above or as resulting from the following description, taken with reference to the drawings which represent an integral part of this invention and illustrate the description.

As will be readily understood by those skilled in the art, this invention covers all characteristics which appear to be novel on the basis of the description taken in its entirety together with the drawings which represent an integral part of the invention, with respect to any background art, as much as a general means and in its general function.

According to a fourth aspect, this invention also covers a fixation and anchoring kit characterized in that it includes at least one surgical device forming a surgical prosthesis, according to one of the preceding aspects, together with an introducer instrument, advantageously in the form of a penetrating trocar, with a protective sheath for the fixation or anchoring system mounted in a compact way or folded back between the penetrating trocar and the sheath, and joined to said sheath at least in the direction of penetration, said sheath including a system to prevent retrocession of the fixation system in place between the trocar and the sheath.

According to a fifth aspect, this invention also covers a surgical method to provide support for an organ which requires support, characterized in that it comprises:

a) local anesthesia administered close to the organ requiring support;

b) incision, and dissection of the tissue opposite and on either side of the said mammalian organ requiring support;

c) insertion of the introducer instrument into the opening created by said incision and dissection of the tissues on one side and behind the organ requiring support, and after said mammalian substrate which is relatively resistant to tearing (e.g. bone or some other appropriate tissue) has been reached, withdrawal of the protective sheath;

d) withdrawal of the penetrating trocar, notably of its needle part;

e) simultaneous pulling on both ends of the advantageously filiform traction component to install the fixation or anchoring system in the correct place and open or deploy it, and advantageously, in the preferred embodiment, to induce the kinking at a minimum of two points of the bridging limbs to allow a so-called umbrella-type positioning with a broad surface of fixation or anchoring of the anchoring system;

f) repetition of preceding steps c), d) and e) on the other side of the organ in order to introduce a second fixation system, preferably identical to the first;

g) passage of one end of the traction component of the first fixation system in a means of joining such as a hole in one first end of the first elongated sling then into the sliding component such as ring or loop of the other end of the filiform traction component, in such a way as to create a lasso-like loop, and a first pulling movement on the end or free part of the traction component for preliminary positioning;

h) repeat of the same procedure as in the preceding step for the second fixation system on the other side of the organ requiring support, thereby preliminarily positioning the elongated sling near the organ in question;

i) simultaneous pulling on both ends or free parts respectively of the first traction component and of the second traction component until there is tension being exerted on the first elongated sling in the correct position in contact with said organ to provide the desired support for said organ;

j) joining of the free ends respectively of the first filiform component and the end of the second filiform component in the ideal position, this joining of said end being carried out at such a position that the organ being supported is not compromised in any way;

k) closure of the incision with a suitable means of surgical closure such as resorbable thread;

According to a preferred embodiment of this surgical procedure, it is used to correct incontinence in female mammals, in particular human females. In this context, the organ to be supported is the urethra, preferably the part of the urethra close to the bladder. In this context, it is preferred according to this invention that the anchoring systems are inserted on tissue of the wall of the pelvic cavity, preferably substantially transversal tissues of the pelvic wall in the part located between the urethra and the flank of the female mammal, in particular a human female, above the vaginal wall.

IN THE DRAWINGS

FIG. 1 shows from above a split diagram of the three main components of the surgical instrument forming a surgical prosthesis, including: at least one first sling with an elongated configuration (e.g. a strip); at least one first fixation or anchoring system including a cage-forming component; and at least one first traction component, advantageously filiform, preferably forming a lasso-like loop device as seen in FIG. 1 in which two bridging arms (48) are indicated by broken lines;

FIG. 3 shows a diagrammatic representation of the deployed fixation or anchoring system, after withdrawal of both the protective sheath and the penetrating trocar and the first pulling on the two ends of the filiform traction component to kink the anchoring system with insertion on the substrate which is relatively resistant to tearing (e.g. bone or some other appropriate tissue);

FIG. 4 shows a cross-section through the line IV-IV in FIG. 3; and

FIG. 5 shows, according to the currently preferred surgical application, a mammalian organ being supported, specifically for the correction of female incontinence with the urethra being supported.

Figure 1:
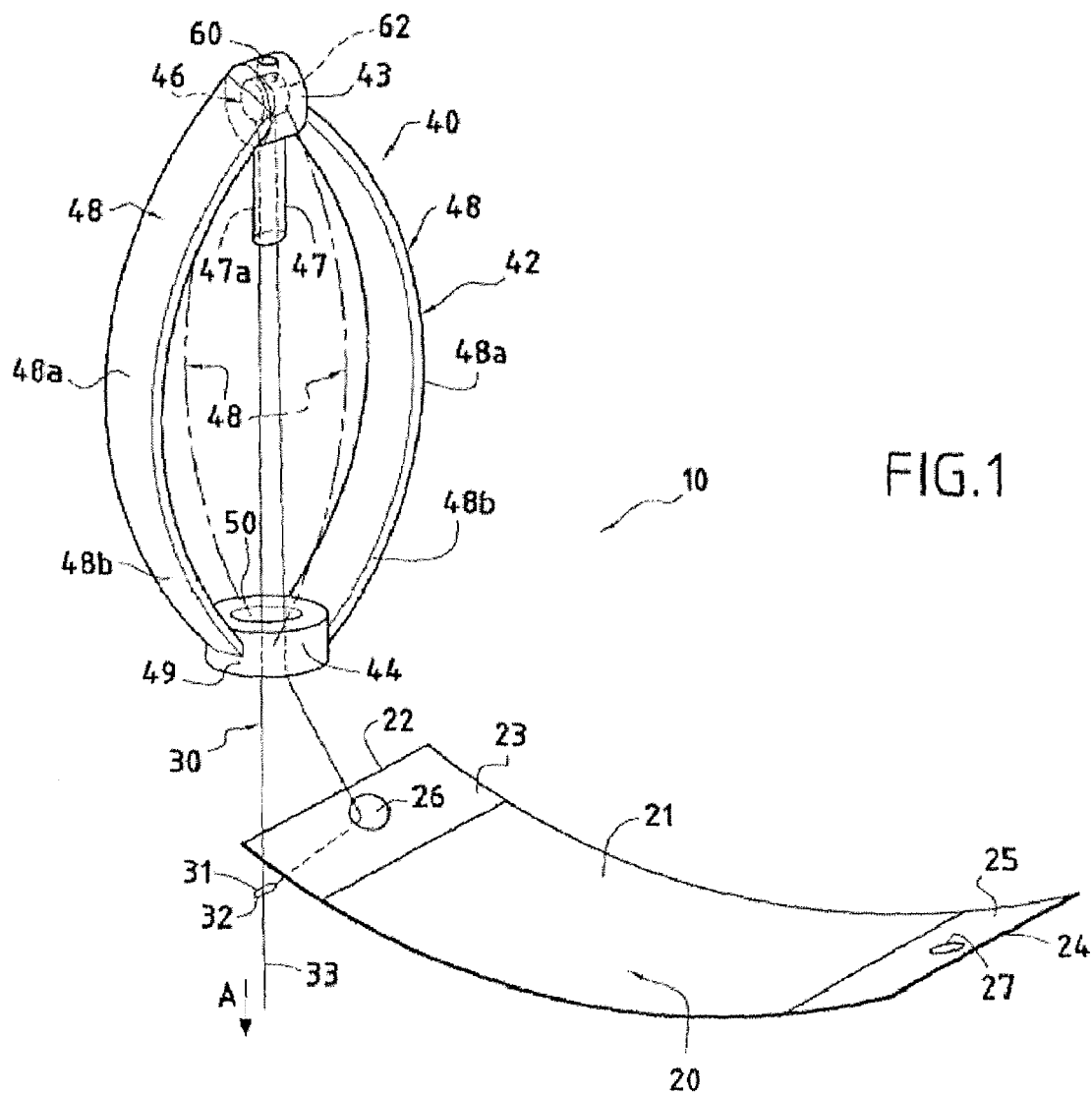

Referring to FIG. 1, a surgical instrument forming a surgical prosthesis according to this invention is represented by the general reference number (10). This is designed to support a physiological mammalian organ requiring such support. The preferred embodiment represented is specifically intended for the correction of urinary incontinence, particularly urinary incontinence in female mammals, and preferably in the human female.

This device (10) is characterized in that it comprises:

a) at least one first support component represented by the general reference number (20), elongated in shape defining a first end (22) and a second end (24). This first support component (20) is designed to exert a supporting action on a physiological mammalian organ requiring support such as the urethra, as shown in FIG. 5.

This first support component (20) is made at least partly of a material which is inextensible but flexible and deformable. Preferably, it is entirely made out this inextensible material.

b) at least one first traction component (30), advantageously filiform, e.g. including a wire or a torus formed by several wires, which can be joined at least temporarily to at least one end (22 or 24) of said first elongated support component. This first traction component (30) can be made of a substantially inextensible material which can pull the elongated sling component (20) and keep it in a position in which it provides said support, as is easily understood from the preceding and following descriptions with reference to FIGS. 3 to 5.

c) at least one first fixation or anchoring system represented by the general reference number (40), designed to work in concert with said first traction component (30), inextensible, in such a way as to fix said first elongated sling component (20) and keep said sling component (20) in the correct position.

The anchoring system (40) preferably includes a cage-forming component represented by general reference number (42) which includes an upper part (43) and a lower part (44), the upper part (43) being fitted with a sliding component (46) to facilitate pulling of the traction component (30) which acts on the elongated sling component (20), in order to effect by means of said pulling the translation of one end (22 or 24) of the elongated sling component in order to support said organ and subsequently keep it in the correct position.

According to a particular modified embodiment of the invention as shown, the first elongated support component (20) or sling is in the shape of a strip (21), with at least the part between its ends consisting of a fabric or meshwork created from one or more wires made of a substantially inextensible but flexible and deformable material. Those skilled in the art are familiar with the production of such strips which is described in the documents cited in the prior art. Particular reference could be made to document WO 98/35632 which describes various alternative embodiments, with areas of reinforcement generated by folding back of the ends as shown in FIG. 6 (FIGS. 6A to 6O), or in FIGS. 7 to 9 in this document.

The dimensions of the strip are also described in detail in the prior art, notably in document WO 98/35632 (from page 7, line 22 to page 15, line 33).

In the context of the present invention, the material used to make the wire or wires comprising the fabric or the strip is preferably an organic polymer which is compatible with implantation in mammalian tissue, this organic material being advantageously one of the group of polyethylene, polypropylene or nylon and preferably polypropylene.

In the context of the invention, the ends (22 and 24) advantageously include at least one area of reinforcement such as (23), (25) formed by a different kind of weave, either advantageously of a single or preferably of at least two folds of the strip back upon itself in such a way as to provide a double or even a triple thickness. Then, means of joining—if only temporary—could be created with the traction components (30) such as an opening respectively (26, 27) for each end (22, 24).

In the context of the invention, according to an advantageous embodiment—which is patentable in and of itself—the traction component (30) is in the form of a traction wire, preferably including a sliding component (32) such as a ring or a loop at one end (31) formed by means of creating a node on the appropriate wire. The other end of the wire (33)—the free end—can be inserted into this ring or loop in such a way as to create a lasso-like loop device as would be easy to understand for those skilled in the art, thereby facilitating pulling on the elongated sling (20) as is explained below. In this case, as has already been described, the sling contains at least one opening (26 or 27) through which the traction wire (30) can be inserted in such a way that the corresponding end—here (21) in FIG. 1—of the sling (20) is trapped by the lasso-like device. Thus, by pulling on the other end or free part (33) in the direction of the indicated arrow A, the translation of the end (22) of the sling (20) (e.g. a strip as here) can be effected.

The anchoring system (40)—which is patentable in and of itself—will now be described in greater detail. This includes a cage-forming device (42) which according to a preferred embodiment includes at its upper end (43) a sliding component (46) which could for example be formed by a hollow, tubular component (47), one end of which (47*a*) is designed to be joined to or continuous with (as shown) said upper part (43) of the cage (42) and, at the same time, to form said sliding component (46), in particular by presenting a surface which forms the displacement or sliding pulley around which the previously mentioned traction wire (30) is designed to slide, as shown in FIG. 1. The end (47*a*) here is continuous with the upper end (43) which also contains a throat (62) forming a surface over which the sliding component (46) can move. The end (47*a*) contains a hole (60) which is coaxial with the hollow tubular component (47), the whole here constituting a single unit which includes the upper end (43) of the cage (42).

Thus, the opening (60) of the upper end (43) of the cage-forming device (42) is specifically designed to receive the needle (113) of the trocar-forming introducer device described below with reference to FIG. 2. Those skilled in the art will also understand that the opening is coaxial with the hole defined by the hollow tubular component (47), so that it can be used to guide the needle (113) of the trocar-forming introducer device, as will also be described with reference to FIG. 2.

Figure 2:
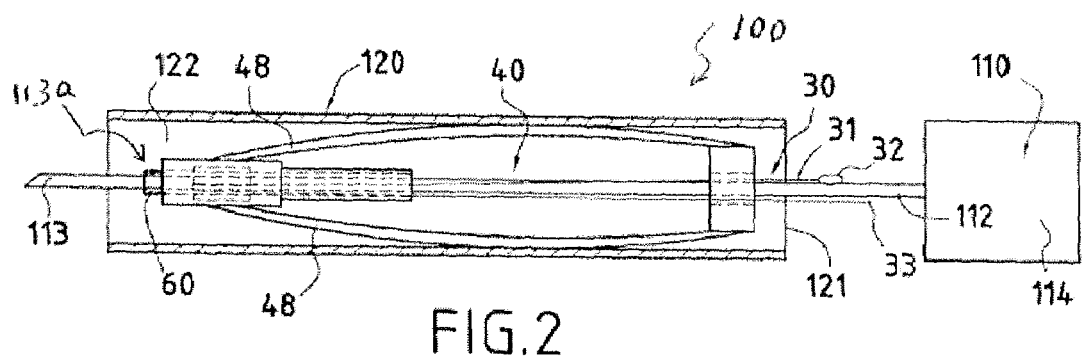
FIG. 2 shows the first fixation or anchoring system fitted with at least one first traction component, advantageously filiform, in place on a penetrating trocar, with an external protective sheath for surgical positioning.

According to an advantageous embodiment of the invention, the upper part (43) and the lower part (44) of the cage (42) are joined to one another by several lateral bridging arms (48), e.g. four such arms as in FIG. 2 where two of the arms are represented by broken lines. These arms—like the rest of the cage and all the other components of the invention—are made of some physiologically compatible, inextensible material. This material is preferably a biocompatible organic material advantageously one of the group of polyethylene, polypropylene or nylon, and preferably polypropylene Advantageously, the length of the bridging arms (48) is such that they readily kink when the traction component (30) is pulled, the beginning of this kinking process being shown in the diagram in FIG. 1. The kinking usually occurs around the mid-point (48*a*) of the arm (48), as will be evident to those skilled in the art. This makes it possible (as shown in FIGS. 3 and 4) to obtain umbrella-like deformation of the anchoring device in which the lower parts of the arms below the kink point (48*a*) create an extensive surface for insertion of the anchoring device on the substrate tissue, thereby reducing or even preventing tearing thereof, as will be explained below.

According to the shown, preferred embodiment, the lower part (44) of the anchoring device (40) is ring-shaped (49) with a central hole (50) through which the two parts of the lasso-like wire can be passed. Obviously, the ring shape is not limiting and diverse configurations are possible. Advantageously, the lower part should be relatively solid in order to constitute a solid base to facilitate kinking of the lateral bridging arms (48).

FIG. 2 shows the introducer device (100) which on one side includes a penetrating trocar (110) made up of a needle (112) with a tapered distal part (113), and a flaring proximal part (114) which forms a shoulder for pushing. This introducer device (100) also includes an external sheath (120) as is classic in trocar introducer systems. The diameter of this sheath is sufficiently larger than that of the needle (112) to create a chamber (122) to accommodate the anchoring device (40) in a folded configuration, pre-fitted with the traction component (30) with its first end (31) including the ring-shaped or looped sliding component (32), and the second free end (33), the two ends projecting out from the sheath far enough to be accessible to the surgeon once the introducer device has been introduced to the desired deployment position, generally above a support such as, for example, the transverse wall of the pelvic cavity (150) as shown in FIG. 4. The rear part of the sheath could advantageously include a compression component (121) such as a screw designed to fix the sheath to the needle (112) during its advance, and create a means of preventing retrocession of the anchoring device (40). This type of introducer device based on a penetrating trocar and a sheath is familiar to surgeons. The needle (112) is advantageously hollow and curved, and includes a bump or stop block (113a) a few centimeters from the distal end designed to prevent retrocession of both the anchoring device (40) when in position, and the needle (112) in the sheath (120). This short needle (112) includes at its proximal end the flared portion or shoulder (114) which is advantageously designed—for example—to receive a syringe for the injection of anesthetic, the flaring making it possible for the operator to take hold of the needle so that it can be directed accurately, the importance of which is evident to surgeons.

"FIGS. 3 and 4 give a representation of the end of the first stage of the installation of the anchoring device (40) which has been deployed by removal first of the sheath and then of the needle (112). Also represented diagrammatically is the end (22) of the sling (20) with the traction component (30) A first end of the wire (31) of the latter (30) has been passed through the hole (26), and the other end of the wire (33) has been inserted in the ring-shaped or looped sliding component (32) in such a way as to form a lasso-like loop, as can be seen clearly in FIG. 3 and as was shown previously in FIG. 1. Pulling on both ends of the traction component (30) at the same time induces the positioning and opening of the anchoring device (40) in a so-called umbrella configuration, with kinking substantially at the midpoint (48a) of each bridging arm (48) in such a way that the lower parts (48b) of the arms (48) constitute together a broad support surface and therefore provide solid anchoring of the anchoring system (40), without exerting any substantial shearing force on the substrate tissues and therefore not leading to tearing of said tissues. Those skilled in the art will understand that to provide the support to an organ that needs such support such as the organ (200) shown in FIG. 5, here the urethra (202) according to the currently preferred application, the operator will have to install-using the introducer device (100)-two fixation systems (40a and 40b), one on either side of the organ requiring support (200), here the urethra (202)"

The operator will also have to trap each end (22 and 24) of the sling (20) (e.g. a strip [21]) in the lasso system, as shown in FIG. 5, and then pull, initially on the two ends of the traction component (33a and 33b) for each anchoring system (40a and 40b) in such a way as to deploy and induce the kinking of the fixation systems (40a and 40b), here in a so-called umbrella configuration, in order that said fixation systems (40a and 40b) are properly inserted on the substrate tissues which corresponds in the case shown to the transverse walls of the pelvic cavity (150) (see FIG. 4) opposite either side of the organ requiring support (200). This insures that the desired supporting role is correctly mediated, as will be readily understood by those skilled in the art, notably stemming from knowledge of the prior art as reported in the documents cited in the paragraph on the background art presented at the beginning of this description.

At the end of the pulling operation, the operator pulls each end (22 and 24) of the sling (20) (e.g. a strip) and when sufficient supporting traction force is being provided, the two free ends (33a and 33b) of each traction component (30a and 30b) are knotted, e.g. using a solid knot (210) which is preferably located outside of the support zone for the organ (200), such as the urethra (202) as shown in FIG. 5.

This invention makes it possible to perform the corrective surgery in an outpatient context with simple local anesthesia.

In the context of the treatment of incontinence in female mammals, in particular the human female, a simple douche and routine vaginal hygienic measures suffice for pre-operative preparation. Neither pre-medication nor per-operative infusion are necessary. Simple oral antibiotics suffice for prophylactic treatment.

With the patient in the gynecological position with her hips flexed at an angle of between 40 and 60°, the operator carries out the surgical procedure described above and also claimed. This surgical procedure includes local anesthesia with about 20 cm$^3$ of 0.5% Xylocaine on the vaginal mucosa at about one centimeter from the meatus, then laterally, and finally beyond the pelvic wall for hydrodissection. The operator will then make a 1-centimeter incision at a distance of one centimeter from the meatus.

Then para-urethral dissection is performed using scissors over three centimeters as afar as the pelvic wall on the right and the urethra on the left.

Then the introducer device is manually inserted under the intravaginal guidance of the fingers of the free hand. Through the incision, while advancing laterally in the detached tissue, the operator exerts mild pressure to broach the pelvic wall (150), then advances a further two centimeters without exerting any force.

Then the sheath (120) is retracted followed by the trocar (110).

Simultaneously pulling on both ends (31 and 33) of each traction component (30) causes the anchoring device (40) to open like an umbrella, then after the end (31) has been passed through the hole (26) in the first sling (20) and the lasso-like loop has been created, as shown in FIG. 3, pulling on the end (33, 33a or 33b) (see FIGS. 3 and 4) induces traction and the elongated sling (20) can be correctly positioned. It should be noted that for certain forms of surgery involving larger organs in the treatment of certain diseases, it may be necessary to use either more than one elongated sling component (20) or a single, broader elongated sling, at the discretion of the surgeon.

Within the scope of the invention, any mammalian organ which can be supported can be treated using the surgical device according to the invention. The invention is particularly suitable for the support of pelvic organs: the urethra, the bladder, the vagina, the cervix of the uterus, the uterus and the rectum.

It is also understood that the invention includes any means that are technically equivalent to those described as well as any combinations thereof.

The invention claimed is:

1. A surgical device forming a surgical prosthesis, designed to provide support to a physiological, mammalian organ that can be supported, comprising:
   a) at least one first support component to provide support comprising a sling, with a first end and a second end designed to exert a supporting action on said physiological mammalian organ requiring support; said sling being made at least partially of a substantially inextensible but flexible and deformable material;
   b) at least one first traction component, which can be connected at least temporarily with at least one end of said sling support component, made of a substantially inextensible material enabling to pull on the sling support component and maintain same in place in a position providing said support;

c) at least one first anchoring system, designed to cooperate with at least said first traction component, to fix said sling support component and keep same in the correct position;

said first anchoring system comprising a cage-forming device with an upper end and a lower end, the upper end being fitted with a sliding component wherein the sliding component of the anchoring system is configured to act as a pulley, around which the traction component can slide or translate to pull on one end of the sling to provide support to said organ and keep said organ in support position, wherein the upper end and the lower end of the cage-forming device of the anchoring system are joined to one another by a series of lateral bridging arms made of a substantially inextensible but flexible and deformable material being long enough to induce a kinking at the vicinity of their mid-point by pulling on the traction component to allow a so-called umbrella-type positioning with a broad surface of fixation or anchoring of the anchoring system.

2. The device of claim 1, wherein the lower end of the anchoring system is configured to be inserted on or attached to a mammalian substrate which is relatively resistant to tearing.

3. The device of claim 1, wherein the traction component is in the form of a traction wire, having a first end and a second end, comprising a ring or loop at one of said first end and of said second end; the other of said first end and of said second end of the wire, named free end, cooperating with said ring or loop to create a lasso-like loop device to facilitate pulling on the sling.

4. The device of claim 1, wherein a single anchoring system is provided designed to simultaneously pull both ends of the sling.

5. The device of claim 1, wherein the first anchoring system joined to a first end of the sling component is configured to allow fixation at a predetermined, set position, while the second end of the sling is joined to a second anchoring system, thereby allowing displacement of the second end of the sling in order to exert a traction force on the mammalian organ as required.

6. The device of claim 1, wherein the cage-forming device comprises at its upper end a hollow, tubular component having a first end which is designed to be joined to or continuous with said upper end of the cage and, at the same time, to form the sliding component by presenting a surface which forms the pulley around which the traction wire is designed to slide.

7. The device of claim 6, wherein said end of the tubular component has a hole which is substantially coaxial with the hollow tubular component.

8. The device of claim 1, wherein the lower part of at least the first anchoring system or of each anchoring system comprises an annular part defining a central hole through which can be passed the first traction component or each traction component.

9. The device of claim 8, wherein said central hole is designed to accommodate the needle of a trocar.

10. The device of claim 1, wherein the sling is in the shape of a strip having a main part which is located between its ends consisting essentially of a fabric or meshwork created from two or more wires made of a substantially inextensible but flexible material.

11. The device of claim 10, wherein the material of the wires comprising the fabric of the strip is an organic polymer which is compatible with implantation in mammalian tissue.

12. The device of claim 11, wherein the organic material is selected from the group consisting of polyethylene, polypropylene and nylon.

13. The device of claim 1, wherein the second inextensible traction component includes or is constituted of an inextensible traction wire made of an inextensible organic material which is compatible with long-term implantation in mammalian tissue.

14. Traction component of the surgical device forming a surgical prosthesis as defined in claim 1, wherein said traction component is made of a substantially filiform inextensible material, and is connectable at least temporarily with at least one end of the sling to allow the pulling of said sling and keep same in a position providing said support.

15. Fixation or anchoring system of the surgical device forming a surgical prosthesis as defined in claim 1, wherein said anchoring system comprises a cage-forming device with an upper end and a lower end, the upper end being fitted with a sliding component for pulling on the traction component which acts on the sling, in order to effect the translation of one end of the sling in order to provide support to said organ or keep said organ in position.

16. Fixation and anchoring kit comprising at least one surgical device forming a surgical prosthesis as defined in claim 1, together with an introducer instrument, in the form of a penetrating trocar, with a protective sheath for the fixation or anchoring system mounted in a compact way or folded back between the penetrating trocar and the sheath, and joined to said sheath at least in the direction of penetration, said sheath comprising a system to prevent retrocession of the fixation system in place between the trocar and the sheath.

17. A method to provide support for an a physiological mammalian organ which requires support, comprising:

a) performing local anesthesia administered close to the organ requiring support;

b) performing incision, and dissection of the tissue opposite and on either side of said physiological mammalian organ requiring support to create an opening;

c) inserting through said opening at least one first elongated support component or sling with a first end and a second end designed to exert a supporting action on said physiological mammalian organ requiring support; said first elongated component being made at least partially of a substantially inextensible but flexible and deformable material; and then an introducer penetrating trocar instrument having a protective sheath and containing at least a first anchoring system designed to cooperate with at least one traction component, into the opening created by said incision and dissection of the tissues on one side and behind the organ requiring support, and after reaching said mammalian substrate which is relatively resistant to tearing, withdrawal of the protective sheath;

d) withdrawing the penetrating trocar;

e) simultaneous pulling on both ends of the filiform traction component to install the anchoring system in the correct place and open or deploy it;

f) repeating preceding steps c), d) and e) on the other side of the organ in order to introduce a second anchoring system, preferably identical to the first;

g) passing one end of the traction component of the first anchoring system in a means of joining in one first end of the first elongated sling then into the sliding component of the other end of the filiform traction component, to create a lasso-like loop, and a first pulling movement on the end or free part of the traction component for preliminary positioning;

h) repeating the same procedure as in the preceding steps for the second anchoring system on the other side of the organ requiring support, thereby preliminarily positioning the elongated sling near the organ in question;

i) simultaneous pulling on both ends or free parts respectively of the first traction component and of the second traction component until there is tension being exerted on the first elongated sling in the correct position in contact with said organ to provide the desired support for said organ;

j) joining of the free ends respectively of the first filiform component and the end of the second filiform component in the appropriate position, this joining of said end being carried out at such a position that the organ being supported is not compromised in any way;

k) closing of the incision with a suitable surgical closing means;

wherein the first anchoring system is designed to fix said first elongated support component and keep same in the correct position;

said first anchoring system comprises a cage-forming device with an upper end and a lower end, the upper end being fitted with a sliding component, which enables to pull on the traction component, which acts on the elongated support component, to effect through said pulling the translation of one end of the elongated support component to provide support to said organ and keep said organ in support position;

wherein said traction component can be connected at least temporarily with at least one end of said first elongated support component and is made of a substantially inextensible material enabling to pull on the first elongated support component and maintain same in the place in a position providing said support;

wherein the upper end and the lower end of the cage-forming device of the anchoring system are joined to one another by a series of lateral bridging arms made of a substantially inextensible but flexible and deformable material, said arms being long enough to induce a kinking at the vicinity of their mid-point by pulling on the traction component to allow a so-called umbrella-type positioning with a broad surface of fixation or anchoring of the anchoring system.

18. The method of claim 17, which is performed to correct incontinence in female mammals.

19. The method of claim 17, wherein the organ to be supported is the urethra.

20. The method of claim 17, wherein at least one anchoring system is inserted on tissue of the wall of the pelvic cavity.

* * * * *